(12) United States Patent
Joiner

(10) Patent No.: US 7,029,687 B1
(45) Date of Patent: Apr. 18, 2006

(54) NON TOXIC FIRE ANT AND TERMITE PESTICIDE

(76) Inventor: Julie Dorean Joiner, P.O. Box 264, Moyers, OK (US) 74557

( * ) Notice: Subject to any disclaimer, the term of this patent is extended or adjusted under 35 U.S.C. 154(b) by 41 days.

(21) Appl. No.: 10/952,040

(22) Filed: Sep. 27, 2004

(51) Int. Cl.
*A01N 25/18* (2006.01)
*A01N 25/34* (2006.01)
*A01N 65/00* (2006.01)

(52) U.S. Cl. .................. 424/403; 424/41; 424/403; 424/734; 424/754; 424/755

(58) Field of Classification Search ............... 424/403, 424/734, 754, 755, 405, 117, 41
See application file for complete search history.

(56) References Cited

U.S. PATENT DOCUMENTS

| | | | |
|---|---|---|---|
| 4,891,222 A | | 1/1990 | Eichhoefer |
| 5,118,506 A | | 6/1992 | Eichoefer |
| 6,531,163 B1 | * | 3/2003 | Bessette et al. ............ 424/747 |
| 6,699,489 B1 | | 3/2004 | Driscoll, Sr. |

FOREIGN PATENT DOCUMENTS

| | | | |
|---|---|---|---|
| WO | WO 97/14309 | * | 4/1997 |
| WO | WO 99/22751 | * | 5/1999 |

OTHER PUBLICATIONS

Nebergall, W. H. et al., General Chemistry. United States of America, D. C. Heath and Company, 1959, pp. 6-10 and 20-21.*

RainDance Water Systems, Inc., "Welcome to RainDance Water Systems", JavaScript Source, 1996.*

Minnesota Department of Health Fact/Sheet Brochure, "Why Does My Water Smell Like Rotten Eggs? Hydrogen Sulfide and Sulfur Bacteria in Well Water", (1998).* http://receipes.alastra.com/marinades/chicken26.htm (2005), "Hot & spicy marinade for grilled chicken recipe", Jun. 6, 2005.* http://www.recipeLand.com/recipe/33802, (1996-2004). "Spicy Hot Caribbean Marinade, #44781", recipe by Sue L., Jun. 6, 2005.* http://www.recipezaar.com, (2005). "Hot and Spicy Chairman's Chicken", Jun. 6, 2005.*

Matsumoto, Y. Const. Insect Behav. Nutur. Prod., Pap Semin (1970), Meetingb Date 1968, 133-60. Volatile organic sulfur compounds as insect attractants with special references to host selection.*

Noble, R. et al. Hortscience (Jun. 1999), 34(3): 554-555. Toxicity of Indian mustard (*Brassica juncea*) and allyl isothio-cyanate to masked chaffer beetle larvae.*

Water Quality Report—Provided by Pushmataha County Extention Office. Testing done by OSU.

Report done for Julie Joiner on home water well. Report dated Dec. 1, 2003.

* cited by examiner

*Primary Examiner*—Michele Flood

(57) ABSTRACT

A pesticide consisting of a mixture of sulfur well water and seven edible ingredients, which becomes lethal to fire ants and termites when mixed together, in a liquid, granular, spray or paste form.

12 Claims, 1 Drawing Sheet

NON TOXIC FIRE ANT AND TERMITE PESTICIDE

BACKGROUND OF THE INVENTION

1. Field of the Invention

This invention relates to a pesticide which has as it's primary focus the control and eradication of fire ants and particularly fire ants of the species *solenopsis invicta*. It is also equally effective in the eradication of termites. This invention is non-toxic to humans, biodegradable and environmentally safe.

2. Description of the Related Art

For over 60 years now there has been a need to control the spread of black and red imported fire ants. They are invading ever-increasing areas of the United States. With each passing year they spread further north, east and west affecting more States. It has been estimated that red imported fire ants cause more than three hundred million dollars worth of damage per year to the State of Texas alone.

Fire ants are omnivorous, feeding on almost any plant or animal matter. Fire ants damage young plants by gnawing holes in roots, tubers, stalks, and buds. The fire ant population has increased so rapidly that they are responsible for the major destruction of crops such as soybeans, potatoes and other vegetables in the farming regions of the United States where they have taken over. They have had a major impact on ground nesting animals and they are a menace to both humans and domestic animals alike. Their venom can cause health problems for humans who are hypersensitive to their venom.

One approach, which has been employed to control the fire ant is chemical pesticides. While these have had minimal success, they also pose environmental hazards. The government has imposed restrictions on some chemicals in an effort to protect the environment from the harmful toxic effects these chemicals produce. Among the chemicals banned or restricted in use by governments are: DDT, Chlordane, Lindane, Aldrin, Heptechlor, Dieldrin, and Mirex. Mirex was found to be one of the most effective fire ant killers, however since its use has been banned in the United States, the fire ant population has increased rapidly.

There are still a number of commercial pesticide products on the market currently. These pesticides are typically contact poisons and are effective in killing a wide variety of insects. One which specifically targeted fire ants is AMDRO (registered trademark of American Cyanamid Company). This product is a delayed-action pesticide advertised to be effective against fire ants because it is eventually ingested by the queen. When the queen is killed, the colony vanishes and the mound is destroyed. However, AMDRO has a number of drawbacks. AMDRO loses much of it's effectiveness following contact with rain or humidity. This is a serious shortcoming, since much of the domain of imported fire ants is along the southern coastal states of the United States where rainfall is plentiful. AMDRO also has a short shelf life after the container has been opened.

Many of the commercial pesticides carry a warning label that they are hazardous to humans and some, such as Orthene (manufactured by The Ortho Group), state that protective gloves should be used when handling. With this in mind some patents have been issued to inventors for fire ant pesticides which contain natural ingredients such as pine oil and even animal waste. For example: U.S. Pat. No. 4,891,222 to Eichhoefer, Jan. 2, 1990, and U.S. Pat. No. 5,118,506 also to Eichhoefer, Jun. 2, 1992 both contain pine oil as one of the major ingredients. U.S. Pat. No. 6,699,489 to Driscoll, Mar. 2, 2004, uses animal waste along with other ingredients. A need still remains though for a product which is both effective against fire ants and termites and at the same time is non-toxic to humans, biodegradable and environmentally safe.

BRIEF SUMMARY OF THE INVENTION

It is an object of this invention to produce a product which is economical, easy and safe to use, and which is effective in killing and controlling fire ants and termites.

A further object of this invention is to produce a product which is environmentally safe and will be easily assimilated into the environment with no adverse effects.

Another object of this invention is to use ingredients which are edible to humans but when combined in a certain manner become toxic to tire ants and termites.

It is still a further object of this invention to provide various compositions and methods for use of this product which kills fire ants and termites, which compositions are preferably in liquid form, but which can also be in granular, spray, or paste form.

A further object of this invention is to provide a product which can be used year round and, in a granular state, can be used as a barrier to prevent ants of all kinds from entering homes or commercial buildings.

This invention is a new product which is made solely from ingredients edible to humans but when cooked and combined together in a certain manner becomes lethal to fire ants and termites.

I have made numerous tests using this new product on fire ant mounds in and around the Moyers, Okla., area. When I tested this product on tire ant mounds, by pouring the liquid on the mound, I observed the following: During the first 20 minutes ½ to ⅔ of the fire ants died as a result of contact with the product. Fire ants were seen trying to flee the mound carrying their eggs. Within 24 hours the mound was completely abandoned. When eggs are removed from the mound they die. Without the worker ants to feed the queen she also dies.

I gave a sample of this product to Mr. Merle Redman who, at the time, worked at the county extension office in Antlers, Okla., which is in Pushmataha County Oklahoma. Mr. Redman also tested this product and observed the same results, that the mound was completely abandoned in 24 hours.

DRAWINGS—REFERENCE NUMERALS

Figure 1:
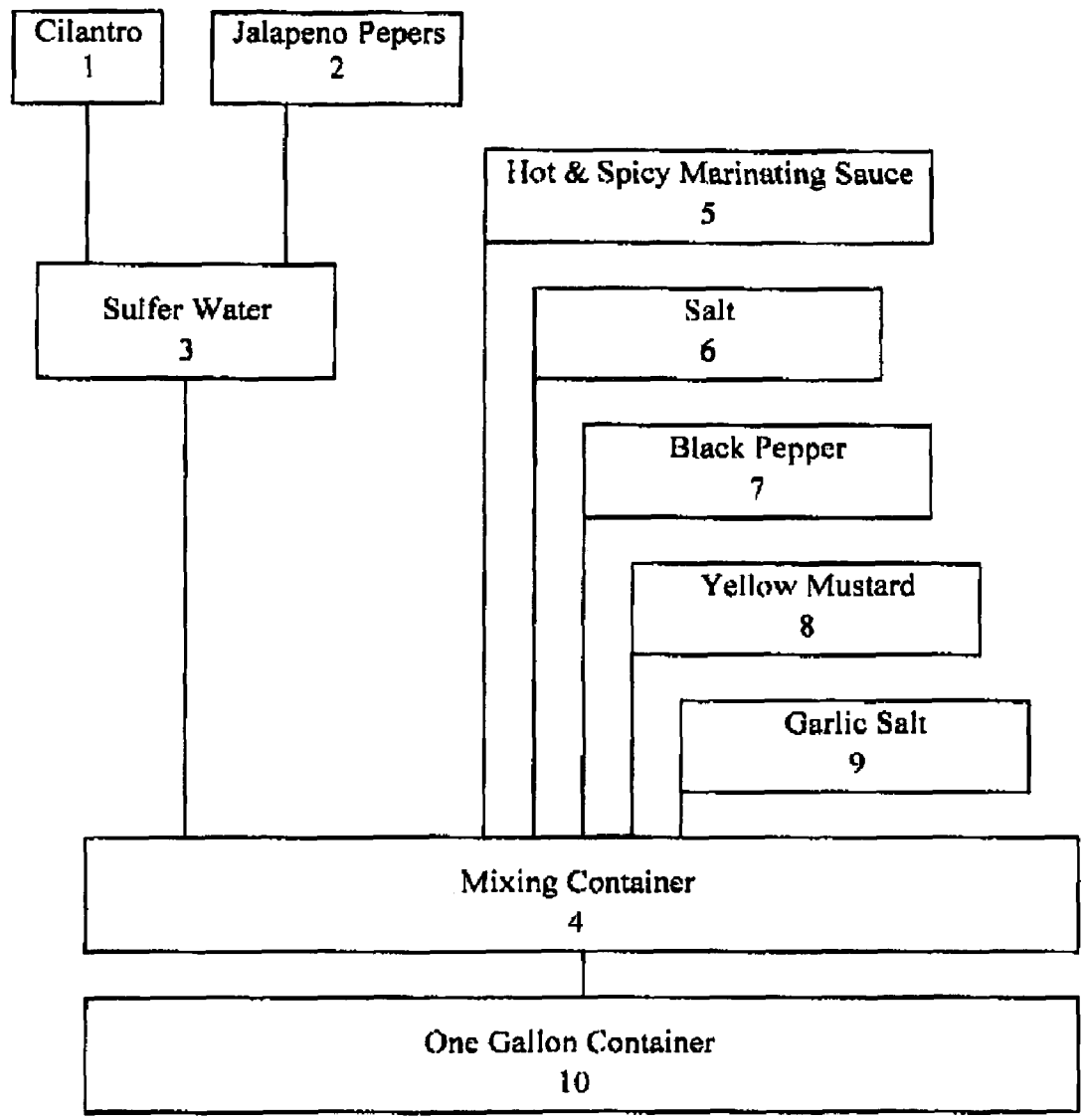
FIG. 1 is a block flow diagram of the ingredients and the method for producing the product comprising the present invention, which method is described in further detail under DETAILED DESCRIPTION OF THE INVENTION.

1. Cilantro
2. Jalapeno Peppers
3. Cooking Pot containing 48 ounces of Sulfur Well Water
4. Second container, that ingredients are mixed in.
5. Hot and Spicy Marinating Sauce
6. Salt
7. Black Pepper
8. Yellow Mustard
9. Garlic Salt
10. One Gallon Container

DETAILED DESCRIPTION OF THE INVENTION

The present invention avoids the problems of previously mentioned chemical pesticides, which can harm the environment and are hazardous to handle, by using ingredients which are edible to humans and environmentally safe but when used in the manner to be described are lethal to fire ants and termites. I have discovered, through extensive experimentation, a product which will both eradicate fire ants and termites and, in a granular form, can be used as a barrier to prevent all types of ants from entering homes or commercial buildings.

The product of this invention is an eight component concentrate which when applied to fire ant mounds and the locus of termites in the manner to be described, results in eradication of fire ants and termites. The concentrate consists of sulfur well water and seven edible ingredients which can be purchased at any grocery store. The preferred formulation of the concentrate and the specifications of each of it's components are set out below.

Looking at the flow chart, you can make 1 gallon of the product by taking 3 ounces of Cilantro 1 and 4 ounces of chopped Jalapeno Peppers 2 and place them in a container with 48 ounces of Sulfur Well Water 3. You cook the Cilantro 1 and Jalapeno Peppers 2 for 20 to 30 minutes in the container with Sulfur Well Water 3, bringing the mixture to a boil. Then you pour the liquid through a strainer into a second mixing container 4. To this you add the other five ingredients: 4.2 ounces of Hot and Spicy Marinating Sauce 5: 13 ounces of Salt 6; 1.3 ounces of Black Pepper 7; 6.6 ounces of Yellow Mustard 8; 3.6 ounces of Garlic Salt 9 and mix together; then you pour 32 ounces of the mixed ingredients into a 1 gallon container 10; and then fill the gallon container the rest of the way up with 96 ounces of Sulfur Well Water. Larger quantities of the product can be made by mixing the ingredients proportionately.

This product has an unlimited shelf life and may be poured or sprayed on the fire ant mound or injected into the mound by means of a hollow probe with numerous outlet holes. The product may also be poured or sprayed on the locus of termites.

It should be recognized that there are other formulations involving differing proportions of the prescribed ingredients which will produce the desired end result of eradicating fire ants and termites.

I claim all modifications and variations coming within the spirit and scope of the following claim/claims.

I claim:

1. A composition for controlling fire ants and termites consisting of a mixture of sulfur well water and the following seven edible ingredients: cilantro, jalapeno peppers, salt, black pepper, yellow mustard, garlic salt, and hot and spicy marinating sauce, which becomes lethal to fire ants and termites when mixed together, in a liquid, granular, spray or paste form.

2. A composition in accordance with claim 1 wherein 1 gallon of the composition contains a mixture of sulfur well water and 3 to 6 ounces of cilantro, 4 to 8 ounces of chopped jalapeno peppers, from 13 to 26 ounces of salt, from 1.3 to 4 ounces of black pepper, from 6.6 to 13 ounces of yellow mustard, from 3.6 to 12 ounces of garlic salt, and from 4.2 to 13 ounces of hot and spicy marinating sauce which consists essentially of: soy sauce, water, salt, hydrolyzed soy protein, corn syrup concentrate, lime juice and caramel coloring.

3. A composition in accordance with claim 1 wherein the mixture is a liquid.

4. A composition in accordance with claim 1 wherein the mixture is a granular form.

5. A composition in accordance with claim 1 wherein the mixture is a spray.

6. A composition in accordance with claim 1 wherein the mixture is a paste.

7. A method for controlling fire ants and termites which comprises applying a pesticidally-effective amount of a composition which contains a mixture of: sulfur well water and the following seven edible ingredients: cilantro, jalapeno peppers, salt, black pepper, yellow mustard, garlic salt, and hot and spicy marinating sauce, which becomes lethal to fire ants and termites when mixed together, in a liquid, granular, spray or paste form, to a locus containing the fire ants or termites.

8. A method in accordance with claim 7 wherein 1 gallon of the composition contains a mixture of sulfur well water and 3 to 6 ounces of cilantro, 4 to 8 ounces of chopped jalapeno peppers, from 13 to 26 ounces of salt, from 1.3 to 4 ounces of black pepper, from 6.6 to 13 ounces of yellow mustard, from 3.6 to 12 ounces of garlic salt, and from 4.2 to 13 ounces of hot and spicy marinating sauce which consists essentially of: soy sauce, water, salt, hydrolyzed soy protein, corn syrup concentrate, lime juice and caramel coloring.

9. A method for controlling fire ants in accordance with claim 7 wherein the mixture is a liquid.

10. A method for controlling fire ants in accordance with claim 7 wherein the mixture is a granular form.

11. A method for controlling fire ants in accordance with claim 7 wherein the mixture is a spray.

12. A method for controlling fire ants in accordance with claim 7 wherein the mixture is a paste.

* * * * *